United States Patent
Boza et al.

(10) Patent No.: US 8,178,487 B2
(45) Date of Patent: May 15, 2012

(54) METHOD FOR PROVIDING GLUTAMINE

(75) Inventors: Julio Boza, La Conversion-Lutry (CH); Olivier Ballevre, Lausanne 25 (CH); Paul-Andre Finot, St-Legier (CH)

(73) Assignee: Nestec S.A., Vevey (CH)

( * ) Notice: Subject to any disclaimer, the term of this patent is extended or adjusted under 35 U.S.C. 154(b) by 292 days.

(21) Appl. No.: 12/277,037

(22) Filed: Nov. 24, 2008

(65) Prior Publication Data

US 2009/0075862 A1 Mar. 19, 2009

Related U.S. Application Data

(63) Continuation of application No. 09/646,748, filed as application No. PCT/EP99/01274 on Feb. 22, 1999, now abandoned.

(30) Foreign Application Priority Data

Mar. 31, 1998 (EP) .................................. 98201016

(51) Int. Cl.
*A61K 38/00* (2006.01)
(52) U.S. Cl. ....................................................... 514/1.1
(58) Field of Classification Search .................. None
See application file for complete search history.

(56) References Cited

U.S. PATENT DOCUMENTS

| | | | |
|---|---|---|---|
| 4,427,658 A | | 1/1984 | Maubois et al. |
| 5,661,123 A | * | 8/1997 | Stalker et al. ...................... 514/2 |
| 5,719,134 A | | 2/1998 | Schmidl et al. |
| 5,849,335 A | | 12/1998 | Ballevre et al. |
| 6,019,999 A | | 2/2000 | Miller et al. |
| 6,051,236 A | | 4/2000 | Portman |

FOREIGN PATENT DOCUMENTS

| | | |
|---|---|---|
| DE | 297 11 429 | 11/1997 |
| EP | 0 418 593 | 3/1991 |
| EP | 0 705 542 | 4/1996 |
| EP | 0 022 019 | 12/2008 |
| JP | 05 065295 | 3/1993 |
| JP | 07 255398 | 12/2008 |
| WO | 98/54985 | 12/1998 |
| WO | WO0215719 | * 2/2002 |
| WO | WO0215720 | * 2/2002 |

OTHER PUBLICATIONS

Boza et al. Nutritional Value and Antigenicity of Two Milk Protein Hydrolysates in Rats and Guinea Pigs. The Journal of Nutrition. 1994. vol. 124, pp. 1978-1986.*
Boza et al. Effects of Native and Hydrolyzed Whey Protein on Intestinal Repair of Severely Starved Rats at Weaning. Feb. 1996, vol. 22, Issue 2, pp. 186-193.*
Boza et al. Nutritional and Antigenic Characterization of an Enzymatic Whey Protein Hydrolysate. J. Agric. Food Chem. 1995, vol. 43, pp. 872-875.*
Boza et al., Clinical Nutrition, vol. 19, No. 5, pp. 319-325, 2000.
Boza et al., Eur. v. Nutr., vol. 39, No. 5, pp. 237-244, 2000.
Costell's Health Distributors Inc. Fall 1997 product catalog which lists the 100% Whey Protein Product (codes 02 288 and 02 289).
Hauser et al., "Plasma Amino Acid Concentrations in Term-Born Infants Fed a Whey Predominant or When Hydrolysate Formula," Journal of Parenteral and Enteral Nutrition, vol. 21, pp. 27-30, 1997.
Raiha et al., "Milk Protein Quantity and Quality in Low-Birthweight Infants: I. Metabolic Responses and Effects on Growth," Pediatrics, vol. 57, pp. 659-674, May 1976.
Rassin et al., "Mil Protein Quantity and Quality in Low-Birth-Weight Infants: II. Effects on Selected Aliphatic Amino Acids in Plasma and Urine," Pediatrics, vol. 59, pp. 407 422, Mar. 1997.
Response to Oral Proceedings of Feb. 25, 2005 and to the observations filed by the patentee on May 12, 2004 dated Sep. 8, 2005.
Rigo et al., "Metabolic balance studies and plasma amino acid concentration in preterm infants fed experimental protein hydrolysate preterm formulas," pp. 98-104, 1994.
Rigo et al., "Nutritional evaluation of protein hydrolysate formulas," European Jounal of Clinical Nutrition, pp. S26-S38, 1995.

* cited by examiner

*Primary Examiner* — Marcela M Cordero Garcia
(74) *Attorney, Agent, or Firm* — K&L Gates LLP

(57) ABSTRACT

A method of providing glutamine to a patient. A nutritional composition which includes whey protein, or a protein mixture which simulates the amino acid profile of whey protein, as a protein source is enterally administered to the patient. The whey protein may be a hydrolyzed whey protein. The patient may be a stressed patient, pre-term baby, or athlete.

14 Claims, No Drawings

METHOD FOR PROVIDING GLUTAMINE

CROSS-REFERENCE TO RELATED APPLICATIONS

This application is a continuation of patent application Ser. No. 09/646,748, filed Dec. 11, 2000, which is a U.S. national stage designation of International application PCT/EP99/001274, filed Feb. 22, 1999, which claims priority to European Patent Application No. 98201016.7, filed on Mar. 31, 1998, the entire contents of which are expressly incorporated herein by reference thereto.

This invention relates to a method for providing glutamine to a human or animal; for example to maintain or increase plasma glutamine levels. The invention also relates to a method for the treatment of humans and animals requiring supplemental glutamine and to a method of increasing glutamine body stores in humans and animals.

The amino acid glutamine has many important functions in the body. For example, glutamine acts as the primary vehicle for transfer of amino nitrogen from skeletal muscle to visceral organs, as a fuel for the rapidly dividing cells of the gastrointestinal tract and immune system, and as a substrate that permits the kidneys to excrete acid loads and protect the body against acidosis. Further, there is increasing evidence that glutamine is essential to the proper functioning of host defense mechanisms and wound healing.

Despite these functions, glutamine is traditionally classified as non-essential amino acid. The reason is that the body is generally able to synthesise sufficient glutamine for its needs from glutamate and glutamic acid. Also, glutamine is the most abundant amino acid in the blood and free amino acid pool of the body. However, this is only true in periods of good health and does not apply to pre-term babies. During periods of illness, the metabolic rate of glutamine increases and the body is not able to synthesise sufficient glutamine to meet its needs. This is particularly true during episodes of stress such as sepsis, injury, burns, inflammation, diarrhea and surgery. During episodes of stress, there is a marked increase in glutamine consumption by the gastrointestinal tract, immune cells, inflammatory tissue and the kidney. This consumption may far outstrip the endogenous rate of synthesis of glutamine. As the deficiency becomes manifest, tissue function alters, morphological changes may be observed, and a negative nitrogen balance arises. Similarly, pre-term babies have a lower rate of glutamine synthesis; often insufficient for needs. Further, it is found that athletes, after intense exercise, have reduced levels of glutamine in their plasma.

The administration of glutamine supplemented diets to pre-term babies, during periods of stress, or to athletes has resulted in improvement of the person's condition. For example, glutamine supplemented diets have been shown to regenerate muco-proteins and intestinal epithelium, support gut barrier function, shorten hospital stay, improve immune function, and enhance patient survival (Stehle et al; 1989; *Lancet,* 1:231-3; Hammerqvist et al; 1989; *Ann. Surg.;* 209: 455-461; Li et al; 1995; *J. Parenter. Enteral Nutr.,* 18, 303-307 and Gianotti et al. 1995; *J. Parenter. Enteral Nutr.,* 19, 69-74). Therefore glutamine is now considered to be a conditionally essential amino acid for critically ill and other stressed patients (Lacey et al; 1990; *Nutrition Review.* 48:297-309).

The additional need for glutamine during periods of stress must come from an exogenous source such as diet. However the supplementation of nutritional formulas with glutamine has traditionally not been performed because glutamine has long been considered to be a non-essential amino acid. Also glutamine is only slightly soluble in water and, more importantly, is relatively unstable in solution. To overcome the stability problem, it has been proposed to supplement powdered formulas with L-glutamine. These formulas are then reconstituted immediately prior to administration. However, for enteral formulas, this approach has not proved to be particularly successful since glutamine in its free form may be converted to pyroglutamate by stomach acids prior to absorption. Also, health care professionals prefer ready-to-consume liquid formulas as opposed to powdered formulas.

Another method of supplementing diet with glutamine has centred on the use of gluten or gluten hydrolysates as a protein source for nutritional compositions. Gluten is particularly rich in glutamine and is hence a good source of glutamine. Also, the use of gluten or a gluten hydrolysate offers the advantage of providing the glutamine in a form which is stable and relatively soluble. However gluten is potentially allergenic and this has severely limited its use in nutritional formulas. This problem may be ameliorated to some extent by using a gluten hydrolysate instead of gluten and a nutritional composition based on gluten hydrolysate are commercially available under the trade names Nutricomp® Immun, Reconvan® and Glutasorb®. However, although the risk from allergenic reaction is much reduced, it has not been removed entirely.

A yet further approach has been to supplement nutritional formulas with synthetic dipeptides such as L-alanyl-L-glutamine or L-glycyl-L-glutamine. These dipeptides are stable in solution and have been shown to be an effective form of glutamine supplementation. However, synthetic peptides of this nature may significantly increase the cost of the nutritional formulas.

Therefore there is a need for an acceptable method of providing glutamine to a patient in need thereof.

Accordingly, in one aspect, this invention provides a method of providing glutamine to a mammal, the method comprising enterally administering to the mammal a nutritional composition which includes whey protein, or a protein mixture which simulates the amino acid profile of whey protein, as a protein source.

It has been surprisingly discovered that the administration of nutritional compositions which contain whey protein, or a protein mixture which simulates the amino acid profile of whey protein, as a protein source increases plasma glutamine levels in humans or animals. This is despite the fact that whey protein contains relatively low amounts of glutamine. Further, nutritional compositions which contain whey protein as a protein source provide glutamine levels much higher than those provided by nutritional compositions containing free amino acids as protein source.

Preferably the patient, human or animal is a stressed patient, pre-term baby, or athlete. Examples of stressed patients are patients who are critically ill, or who are suffering from sepsis, injury, burns, or inflammation, or patients recovering from surgery.

In another aspect, this invention provides a method of increasing the muscular glutamine levels of a mammal, the method comprising enterally administering to the mammal an effective amount of a nutritional composition which includes whey protein, or a protein mixture which simulates the amino acid profile of whey protein, as a protein source.

In a further aspect, this invention provides a method of improving glutamine status of mammals suffering from injured diseased or under-developed intestines or to maintain the physiological functions of the intestine, the method comprising enterally administering to the mammal an effective amount of a nutritional composition which includes whey protein, or a protein mixture which simulates the amino acid profile of whey protein, as a protein source.

The mammal may be a pre-term infant.

Embodiments of the invention are now described by way of example only. The invention is based on the finding that enterally administering a nutritional composition which includes whey protein, or a protein mixture which simulates the amino acid profile of whey protein, as a protein source results in high plasma glutamine levels. This makes the composition extremely useful for nutritionally managing glutamine levels in mammals.

The whey protein in the protein source may be may be in the form of intact protein or may be hydrolyzed protein, or mixtures of intact and hydrolyzed protein. The protein source may, if desired, further include amounts of other suitable types of protein. For example, the protein source may further include minor amounts of casein protein, soy protein, rice protein, pea protein, carob protein, oat protein, caseino-glyco-macropeptide or mixtures of these proteins. Further, if desired, the protein source may further include amounts of free amino acids. The other suitable types of protein preferably comprise less than about 20% by weight of the protein source; more preferably less than about 10% by weight. It is also possible to provide a protein source which simulates the amino acid profile of whey protein. For example, the protein source may comprise about 80% to about 90% by weight of casein, about 0.5 to about 2% by weight of isoleucine, about 2% to about 8% by weight of leucine, about 1% to about 5% by weight of cysteine, and about 1% to about 5% by weight of lysine.

Preferably however, the protein source comprises a whey protein hydrolysate; either based upon sweet whey or acid whey. Whey protein hydrolysates are particularly suitable for patients suffering from compromised gastro-intestinal functions, malabsorption or intolerance. The whey protein hydrolysates may be produced using procedures which are well known in the art. Alternatively, nutritional compositions which contain whey protein hydrolysates may be obtained commercially. For example, clinical nutritional compositions containing whey hydrolysates are commercially available from Nestlé Nutrition Company under the trade mark PEPTAMEN®, or Nutrition Medical, Inc under the trade mark PROPEPTIDES®. Similarly, infant nutritional compositions containing whey hydrolysates are commercially available from Nestlé Alete GmbH under the trade mark ALFARE®.

For infant applications, the whey protein hydrolysate preferably additionally contains the free amino acids arginine, tyrosine and histidine.

For adult applications, whey protein hydrolysates which have a degree of hydrolysis of about 10% to about 20% are particularly preferred. In this specification, the term "degree of hydrolysis" (DH) means the percentage of nitrogen in the form of amino nitrogen as compared to total nitrogen. It is a measure of the extent to which the protein has been hydrolyzed. Whey protein hydrolysates having a degree of hydrolysis of about 10% to about 20% contain less than about 5% of free amino acids, about 15% to about 55% of peptides having a molecular weight of less than 1000 Da, about 20% to about 55% of peptides having a molecular weight of 1000 Da to 5000 Da, and about 15% to about 35% of peptides having a molecular weight of greater than 5000 Da.

For adult applications, the protein source preferably provides about 10% to about 20% of the energy of the nutritional composition. For example, the protein source may provide about 15% to about 18% of the energy of the nutritional composition. For infant applications, the protein source preferably provides about 50% to about 30% by dry weight of the nutritional composition. For example, full term infant formulas, the protein source may provide about 8% to about 20% by dry weight of the nutritional composition. Further, for pre-term infant formulas, the protein source may provide about 15% to about 25% by dry weight of the nutritional composition.

The nutritional composition may also include a carbohydrate source. For adult applications, the carbohydrate source preferably provides about 35% to about 65% of the energy of the nutritional composition; especially 40% to 60% of the energy of the nutritional composition. For example, the carbohydrate source may provide about 51% of the energy of the composition. For infant applications, the carbohydrate source preferably provides about 35% to about 70% by dry weight of the nutritional composition; more preferably about 45% to about 65% by dry weight. Several carbohydrates may be used including maltodextrin, corn starch, modified starch, lactose, or sucrose, or mixtures thereof. Preferably the composition is free from lactose.

The nutritional composition may further include a lipid source. For adult applications, the lipid source preferably provides about 20% to about 50% of the energy of the nutritional composition; especially 25% to about 40% of the energy of the nutritional composition. For example, the lipid source may provide about 33% of the energy of the nutritional composition. For infant applications, the lipid source preferably provides about 15% to about 35% by dry weight of the nutritional composition; especially 20% to about 30% by dry weight of the nutritional composition. For example, the lipid source may provide about 26% by dry weight of the nutritional composition.

The lipid source may comprise a mixture of medium chain triglycerides (MCT) and long chain triglycerides (LCT). If MCT's are included, the lipid source preferably contains at least about 30% to about 80% by weight of medium chain triglycerides. For example, medium chain triglycerides may make up about 70% by weight of the lipid source. Suitable sources of long chain triglycerides are sunflower oil, safflower oil, rapeseed oil, palm olein, soy oil, milk fat, corn oil and soy lecithin. Fractionated coconut oils are a suitable source of medium chain triglycerides.

The lipid profile of the nutritional composition may be designed to have a polyunsaturated fatty acid omega-6 (n-6) to omega-3 (n-3) ratio of about 1:1 to about 12:1. For example, for adult applications, the n-6 to n-3 fatty acid ratio may be about 6:1 to about 9:1. For infant applications, the n-6 to n-3 fatty acid ratio may be about 9:1 to about 11:1. Also, for infant applications, the lipid source may include long chain, polyunsaturated fatty acids such as arachidonic acid and docosahexaenoic acid.

The nutritional composition preferably includes a complete vitamin and mineral profile. For example, sufficient vitamins and minerals may be provided to supply about 50% to about 250% of the recommended daily allowance of the vitamins and minerals per 1000 calories of the nutritional composition.

For adult applications, the nutritional composition preferably has an energy content of about 800 kcal/l to about 1200 kcal/l; for example an energy content of about 1000 kcal/l. For infant applications, the nutritional composition preferably has an energy content of about 600 kcal/l to about 1000 kcal/l; for example an energy content of about 650 kcal/l to about 850 kcal/l.

The nutritional composition may be in any suitable form. For example, the nutritional composition may be in the form of a soluble powder, a liquid concentrate, or a ready-to-drink formulation. Alternatively, the nutritional composition may be in solid form; for example in the form of a ready-to-eat bar or breakfast cereal. Ready to drink formulations are particularly preferred. The composition may be fed to a patient via a nasogastric tube, jejunum tube, or by having the patient drink or eat it. Various flavours, fibres, sweeteners, and other additives may also be present.

The nutritional composition may be produced as is conventional; for example, the nutritional composition may be prepared by blending together the protein source, the carbohydrate source, and the lipid source. If used, the emulsifiers may be included in the blend. The vitamins and minerals may be added at this point but are usually added later to avoid thermal degradation. Any lipophilic vitamins, emulsifiers and the like may be dissolved into the lipid source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture.

The liquid mixture may then be thermally treated to reduce bacterial loads. For example, the liquid mixture may be rapidly heated to a temperature in the range of about 80° C. to about 10° C. for about 5 seconds to about 5 minutes. This may be carried out by steam injection or by heat exchanger; for example a plate heat exchanger.

The liquid mixture may then be cooled to about 60° C. to about 85° C.; for example by flash cooling. The liquid mixture is then homogenised; for example in two stages at about 7 MPa to about 40 MPa in the first stage and about 2 MPa to about 14 MPa in the second stage. The homogenised mixture may then be further cooled to add any heat sensitive components; such as vitamins and minerals. The pH and solids content of the homogenised mixture is conveniently standardised at this point.

If it is desired to produce a powdered nutritional composition, the homogenised mixture is transferred to a suitable drying apparatus such as a spray drier or freeze drier and converted to powder. The powder should have a moisture content of less than about 5% by weight. If it is desired to produce a liquid nutritional composition, the homogenised mixture is preferably aseptically filled into suitable containers. Aseptic filling of the containers may be carried out by pre-heating the homogenised mixture (for example to about 75 to 85° C.) and then injecting steam into the homogenised mixture to raise the temperature to about 140 to 160° C.; for example at about 150° C. The homogenised mixture may then be cooled, for example by flash cooling, to a temperature of about 75 to 85° C. The homogenised mixture may then be homogenised, further cooled to about room temperature and filled into containers. Suitable apparatus for carrying out aseptic filling of this nature is commercially available.

The nutritional composition may be used as a nutritional support, especially for providing nutrition and glutamine to animals and humans. In particular, the nutrition composition may be used to provide nutrition and glutamine to stressed patients; for example for patients who are critically ill, or who are suffering from sepsis, injury, burns, or inflammation, or patients recovering from surgery. Further, the nutritional composition may be used to provide glutamine to patients suffering from injured or diseased intestines or to maintain the physiological functions of the intestine. Moreover, the nutritional composition may be used to raise plasma glutamine levels in humans and animals.

The nutritional composition may also be used to provide glutamine to athletes after intense exercise or to pre-term babies.

It is to be understood that, although the nutritional composition is intended primarily for patients who require supplemental glutamine, it may also be used as a source of nutrition for people who are not suffering from any illness or condition.

The nutritional composition may form the sole source of nutrition or form a supplement to other nutritional sources; including parenterally administered nutrition.

The amount of the nutritional composition required to be fed to a patient will vary depending upon factors such as the patient's condition, the patient's body weight, the age of the patient, and whether the nutritional composition is the sole source of nutrition. However the required amount may be readily set by a medical practitioner. In general, sufficient of the nutritional composition is administered to provide the patient with about 1 g protein to about 4.0 g protein per kg of body weight per day. For example, an adult, critically ill patient may be administered about 1.5 g protein to about 2.0 g protein per kg of body weight per day, a pre-term infant may be administered about 2.0 g protein to about 4.0 g protein per kg of body weight per day, and a infant may be administered about 2.0 g protein to about 3.0 g protein per kg of body weight per day. Further, for stressed patients, sufficient of the nutritional composition is preferably administered to provide the patient with about 10 g to about 25 g of glutamine per day. The nutritional composition may be taken in multiple doses, for example 2 to 5 times, to make up the required daily amount or may taken in a single dose. Alternatively, the nutritional composition may be fed to the patient continuously.

Specific examples of the invention are now described for further illustration.

EXAMPLE 1

An isotonic liquid diet which is suitable for raising plasma glutamine levels in a patient is obtained from Nestlé Clinical Nutrition. The diet is commercialised under the trademark PEPTAMEN®. The diet has the following components:

| Nutrient | Amount per 1000 ml |
|---|---|
| Protein (hydrolyzed sweet whey) | 40 g |
| Carbohydrate (maltodextrin, corn starch) | 127 |
| Lipid (medium chain triglycerides, sunflower oil, soy lecithin) | 39 |
| Vitamin A | 4000 IU |
| Vitamin D | 280 IU |
| Vitamin E | 28 IU |
| Vitamin K | 80 µg |
| Vitamin C | 140 mg |
| Thiamin | 2 mg |
| Riboflavin | 2.4 mg |
| Niacin | 28 mg |
| Vitamin $B_6$ | 4 mg |
| Folic acid | 540 µg |
| Pantothenic acid | 14 mg |
| Vitamin $B_{12}$ | 8 µg |
| Biotin | 400 µg |
| Choline | 450 mg |
| Taurine | 80 mg |
| L-carnitine | 80 mg |
| Minerals Calcium, Phosphorus, Magnesium, Zinc, Iron, Copper, Manganese, Iodine, Sodium, Potassium, Chloride, Chromium, Molybdenum, Selenium | |

The diet has an energy density of 1000 kcal/l and the protein provides 16% of energy, the carbohydrate provides 51% of energy, and the lipid provides 33% of energy. Glutamine provides about 6.2% by weight of the protein source.

EXAMPLE 2 i) Test Diets

The following diets are used in the test:

| Diet | Composition | Protein Source | Glutamine Content (g/100 g) |
|---|---|---|---|
| 1 | 95% composition of example 1 and 5% cellulose | Hydrolyzed whey | 6.2 |
| 2 | 95% PROPEPTIDES product and 5% cellulose | Hydrolyzed whey | 5.42 |
| A | 95% VIVONEX PLUS product and 5% cellulose | Free amino acids | 21.63 |
| B | 95% REABILAN product and 5% cellulose | Hydrolyzed casein & whey | 8.09 |
| Control | soy protein isolate, sucrose, glucose, cellulose, corn starch, corn oil and vitamins and minerals | Soy | 8.99 |

The VIVONEX PLUS product is a product obtained from Sandoz Nutrition AG. The REABILAN product is a product obtained from Nestlé Clinical Nutrition.

ii) Test Analytical Procedures

Plasma amino acids are analyzed by de-proteinising 200 µl of plasma using 20 µl of a solution containing sulfosalicylic acid (400 mg/ml) and vitamin C (60 mg/ml). The mixture is centrifuged at 10,000 g for 3 minutes. D-glucosaminic acid and S-(2-aminomethyl)-L-cysteine.HCl are added to the supernatant as internal standards and the supernatant is frozen at −80° C. until analyzed. A Beckman 6300 amino acid analyzer is used for the analysis. To avoid glutamine degradation, all samples are kept at 10° C. before analysis. Amino acid concentrations are calculated for individual peak areas, external standards and the internal standards.

Muscle glutamine is analyzed by mixing 100 mg of muscle with an ice cold solution of trichloroacetic acid (10% w/v) and homogenising the mixture at 10,000 rpm for 1 minute. The mixture is then centrifuged at 10,000 g for 10 minutes at 4° C. D-glucosaminic acid is added to the supernatant as internal standard and the supernatant is frozen at −80° C. until analyzed. A Beckman 6300 amino acid analyzer is used for the analysis. To avoid glutamine degradation, all samples are kept at 10° C. before analysis. Amino acid concentrations are calculated for individual peak areas, external standards and the internal standards.

iii) Test Procedure

Fifty six male Wistar rats, each weighing about 200 g, are used. The rats are held in separate cages at 23° C. A 12 hour dark cycle is imposed. The rats have free access to water and the Control diet.

The rats are maintained on the Control diet for 3 days. On the fourth day, the amount of the Control diet for each rat is restricted to 80% of its consumption on the previous three days. The Control diet is fed to the rats once a day. On the seventh day, the rats are placed in metabolic cages and randomised by weight into 7 groups of 8 rats. One group of rats, the control group, is maintained on the Control diet. The rats in the remaining groups are then starved for 72 hours. All rats have free access to water.

At the end of the starvation period, a 1 ml blood sample is taken from the eye of each rat of one group under anaesthesia; the control starved group. The blood sample is then analyzed for plasma amino acids as described above. The rats of this group are then sacrificed and the muscle tibialis of rat are removed and stored at −80° C. until analyzed for muscle glutamine as described above.

The remaining tests rats are placed into new metabolic cages and are again randomised by weight into five groups of 8.

The five groups are then each fed an experimental diet; the diets differing from group to group. The diets are as follows:

| Group | Diet |
|---|---|
| Control Re-fed | Control |
| 1 | 1 |
| 2 | 2 |
| A | A |
| B | B |

The rats are fed the diets for 3 days. At the end of the three days, a 1 ml blood sample is taken from the eve of each rat of one group under anaesthesia. Plasma samples are then analyzed for plasma amino acid concentrations as described above. The rats are then sacrificed and the muscle tibialis of rats are removed. The muscle is analyzed for muscle glutamine as described above.

iv) Test Results

The plasma glutamine concentrations are as follows:

| Group | Diet | Glutamine Intake (µmol/l) | Plasma glutamine (µmol/l) | Muscle glutamine (µmol/g) |
|---|---|---|---|---|
| Control | Control | 733 | 829.1 | 4 |
| Control starved | Control | — | 758.6 | 2.7 |
| Control re-fed | Control | 734 | 742.5 | 3.6 |
| 1 | 1 | 392 | 1025.6 | 5.3 |
| 2 | 1 | 336 | 1031.1 | 4.9 |
| A | A | 1501 | 738.7 | 3.3 |
| B | B | 424 | 881.7 | 3.9 |

The results indicate that the rats fed diets 1 and 2, the whey protein based diets, have plasma glutamine concentrations of at least 25% higher than the other rats. This is despite the fact that the rats fed diets 1 and 2 received less glutamine in the diet; and significantly less than the free amino acid diet A. Similarly, the results indicate that the rats fed diets 1 and 2 have higher muscle glutamine concentrations; significantly higher than the control rats in the case of diet 1.

Further, the rats fed diets 1 and 2 recovered better after starvation in terms of weight gain, food conversion efficiency, retained nitrogen to ingested nitrogen, retained nitrogen to absorbed nitrogen and protein efficiency ratio.

The invention claimed is:

1. A method for increasing plasma glutamine concentration in a stressed mammal, the method comprising the step of administering to the stressed mammal a nutritional composition having as its sole protein source a protein source having at least 80% by weight of a component selected from the group consisting of whey protein, and a protein mixture which simulates the amino acid profile of whey protein consisting of approximately 80% to about 90% by weight of casein, approximately 0.5% to about 2% by weight of isoleucine, about 2% to about 8% by weight of leucine, about 1% to about 5% by weight of cysteine, and about 1% to about 5% by weight of lysine, wherein the nutritional composition has an energy content from about 600 kcal/1 to about 1200 kcal/1, wherein the whey protein is hydrolyzed whey protein and contains less than about 5% by weight of free amino acids, about 15% to about 55% by weight of peptides having a molecular weight of less than 1000 Da, about 20% to about 55% by weight of peptides having a molecular weight of 1000 Da to 5000 Da, and about 15% to about 35% by weight of peptides having a molecular weight of greater than 5000.

2. The method of claim 1 wherein the protein source provides about 10% to about 20% of the energy of the nutritional composition.

3. The method of claim 1 wherein the nutritional composition further includes a lipid source which provides about 20% to about 50% of the energy of the nutritional composition, the lipid source comprising a mixture of medium chain and long chain fatty acids.

4. The method of claim 1 wherein the nutritional composition further includes a carbohydrate source which provides about 35% to about 65% of the energy of the nutritional composition.

5. A method for increasing muscle glutamine concentrations in a mammal, the method comprising the step of administering to the mammal a nutritional composition having as its sole protein source a protein source having at least 80% by weight of a component selected from the group consisting of whey protein, and a protein mixture which simulates the amino acid profile of whey protein consisting of approximately 80% to about 90% by weight of casein, approximately 0.5% to about 2% by weight of isoleucine, about 2% to about 8% by weight of leucine, about 1% to about 5% by weight of cysteine, and about 1% to about 5% by weight of lysine, wherein the nutritional composition has an energy content from about 600 kcal/1 to about 1200 kcal/1, wherein the whey protein is hydrolyzed whey protein and contains less than about 5% by weight of free amino acids, about 15% to about 55% by weight of peptides having a molecular weight of less than 1000 Da, about 20% to about 55% by weight of peptides having a molecular weight of 1000 Da to 5000 Da, and about 15% to about 35% by weight of peptides having a molecular weight of greater than 5000.

6. The method of claim 5 wherein the protein source provides about 10% to about 20% of the energy of the nutritional composition.

7. The method of claim 5 wherein the nutritional composition further includes a lipid source which provides about 20% to about 50% of the energy of the nutritional composition, the lipid source comprising a mixture of medium chain and long chain fatty acids.

8. The method of claim 5 wherein the nutritional composition further includes a carbohydrate source which provides about 35% to about 65% of the energy of the nutritional composition.

9. A method for providing glutamine to a mammal suffering from injured, diseased or under-developed intestines, the method comprising the step of administering to the mammal a nutritional composition having as its sole protein source a protein source having at least 80% by weight of a component selected from the group consisting of whey protein, and protein mixture which simulates the amino acid profile of whey protein consisting of approximately 80% to about 90% by weight of casein, approximately 0.5% to about 2% by weight of isoleucine, about 2% to about 8% by weight of leucine, about 1% to about 5% by weight of cysteine, and about 1% to about 5% by weight of lysine, wherein the nutritional composition has an energy content from about 600 kcal/1 to about 1200 kcal/1, wherein the whey protein is hydrolyzed whey protein and contains less than about 5% by weight of free amino acids, about 15% to about 55% by weight of peptides having a molecular weight of less than 1000 Da, about 20% to about 55% by weight of peptides having a molecular weight of 1000 Da to 5000 Da, and about 15% to about 35% by weight of peptides having a molecular weight of greater than 5000.

10. The method of claim 9 wherein the mammal is a preterm infant having an under-developed intestine.

11. The method of claim 10 wherein the whey protein is hydrolyzed and the protein source further comprises arginine, tyrosine and histidine.

12. The method of claim 9 wherein the protein source provides about 10% to about 20% of the energy of the nutritional composition.

13. The method of claim 9 wherein the nutritional composition further includes a lipid source which provides about 20% to about 50% of the energy of the nutritional composition, the lipid source comprising a mixture of medium chain and long chain fatty acids.

14. The method of claim 9 wherein the nutritional composition further includes a carbohydrate source which provides about 35% to about 65% of the energy of the nutritional composition.

\* \* \* \* \*